United States Patent [19]

Starkebaum et al.

[11] Patent Number: 5,628,317

[45] Date of Patent: May 13, 1997

[54] ULTRASONIC TECHNIQUES FOR NEUROSTIMULATOR CONTROL

[75] Inventors: Warren Starkebaum, Plymouth; Mark T. Rise, Monticello, both of Minn.

[73] Assignee: Medtronic, Inc., Minneapolis, Minn.

[21] Appl. No.: 627,574

[22] Filed: Apr. 4, 1996

[51] Int. Cl.$^6$ .................................................. A61B 8/12
[52] U.S. Cl. ................... 128/660.03; 128/662.06; 607/48
[58] Field of Search ............................ 607/49, 56, 48; 128/660.03, 662.05, 662.06

[56] References Cited

U.S. PATENT DOCUMENTS

| | | | |
|---|---|---|---|
| 4,044,774 | 8/1977 | Corbin et al. | 128/404 |
| 4,454,764 | 6/1984 | Sorenson | 73/642 |
| 4,458,689 | 7/1984 | Sorenson et al. | 128/660 |
| 4,476,873 | 10/1984 | Sorenson et al. | 128/660 |
| 4,489,729 | 12/1984 | Sorenson et al. | |
| 4,612,937 | 9/1986 | Miller | 128/663 |
| 4,706,681 | 11/1987 | Breyer et al. | 128/642 |
| 5,002,053 | 3/1991 | Garcia-Rill et al. | 607/49 |
| 5,031,618 | 7/1991 | Mullet | 128/421 |
| 5,095,905 | 3/1992 | Klepinski | 128/642 |
| 5,121,754 | 6/1992 | Mullet | 128/786 |
| 5,143,067 | 9/1992 | Rise et al. | 128/642 |

OTHER PUBLICATIONS

Holsheimer, J. et al., "MR Assessment of the Normal Position of the Spinal Cord in the Spinal Canal" *AJNR Am J Neuroradiol* 15:951–959, May 1994.

Rise, M.T., et al., "An Ultrasonic Bladder–Volume Sensor" *IEEE Transactions on Biomedical Engineering*, vol. BME-26, No. 12, Dec. 1979.

Wells, P.N.T., *Physical Principles of Ultrasonic Diagnosis*, "Pulse-Echo Techniques" Chapter/Section 4.3, pp. 97–98.

*Primary Examiner*—Marvin M. Lateef
*Assistant Examiner*—Derrick Fields
*Attorney, Agent, or Firm*—Banner & Witcoff, Ltd.

[57] ABSTRACT

A lead adapted to be implanted adjacent a spinal cord located within a spinal column of a vertebrate in order to facilitate stimulation of the spinal cord or adjacent tissue. An ultrasonic transmitter/receiver produces an ultrasonic sound wave that creates ultrasonic echo waves reflected from a predetermined portion of the spinal cord and generates a distance signal related to the distance between the transducer/receiver and the predetermined portion of the spinal cord. The distance signal is used to adjust the amplitude of an electrical stimulation signal that stimulates the spinal cord or adjacent tissue so that the value of the stimulation signal tends to remain uniform in spite of changes in the relative distance between the transducer/receiver and the predetermined portion of the spinal cord.

12 Claims, 2 Drawing Sheets

ULTRASONIC TECHNIQUES FOR NEUROSTIMULATOR CONTROL

BACKGROUND OF THE INVENTION

1. Field of the Invention

This invention relates implantable techniques for electrical stimulation of an organism, and more particularly, relates to such techniques for electrical stimulation of a tissue adjacent to a spinal column.

2. Description of the Related Art

Electrical leads for electrical stimulation of a spinal cord or tissue adjacent a spinal cord have been made in the past and are disclosed, for example, in U.S. Pat. Nos. 4,044,774; 5,143,067; 5,095,905; 5,031,618 and 5,121,754. Experience has shown that positional sensitivity has continued to be a problem for users of such spinal cord stimulators. Over a period of time, the stimulator may change its position with respect to the spinal column, and such positioning changes adversely affect the stimulation provided by the lead unless there is a corresponding change in the magnitude of the stimulation.

A nerve stimulator sold by Medtronic, Inc. under the name ITREL II has a "magnet amplitude" mode which allows the user to manually toggle the amplitude of the electrical stimulation between pre-programmed high and low amplitude states. U.S. Pat. No. 5,031,618 (Mullett), assigned to Medtronic, Inc., discloses a system that uses a position sensor, such as a mercury switch, to modulate the output of a neurostimulator. Neither of the foregoing systems is capable of measuring the distance between the stimulator electrodes and the spinal cord which is a key parameter affecting stimulation thresholds in the spinal cord. See, "MR Assessment of the Normal Position of the Spinal Cord in the Spinal Canal" by J. Holsheimer, et al., *American Journal of Neuroradiology* (May, 1994).

U.S. Pat. No. 4,706,681 (Breyer et al.) discloses marker transducers which respond to ultrasonic signals to generate electrical signals which localize the marker transducers. However, the transducers do not determine this location with respect to tissue.

SUMMARY OF THE INVENTION

The invention may take the form of apparatus for stimulation of tissue adjacent the spinal cord of a vertebrate. In such an environment, a preferred embodiment of the invention includes an ultrasonic transducer module implanted adjacent the spinal cord for producing an ultrasonic wave that creates a corresponding ultrasonic echo wave reflected from a predetermined portion of the spinal cord. The transducer module also generates a distance signal in response to the ultrasonic echo wave. The value of the distance signal is related to the distance between the transducer module and the spinal cord. A stimulation driver generates a stimulation signal suitable for stimulating the spinal cord or adjacent tissue. A drive amplifier responsive to the stimulation signal and the distance signal generates a drive signal that increases in value as the distance between the transducer module and the spinal cord increases and decreases in value as the distance between the transducer module and the spinal cord decreases. One or more stimulation electrodes can be implanted adjacent the spinal cord, and the drive signal is transmitted to the electrodes so that the uniformity of stimulation received by the spinal cord or adjacent tissue is increased in spite of changes in the relative distance between the transducer module and the spinal cord. By using the foregoing techniques, the accuracy and uniformity of the stimulation provided to the spinal cord or adjacent tissue can be increased even if the transducer module changes position relative to the spinal cord.

BRIEF DESCRIPTION OF THE DRAWING

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
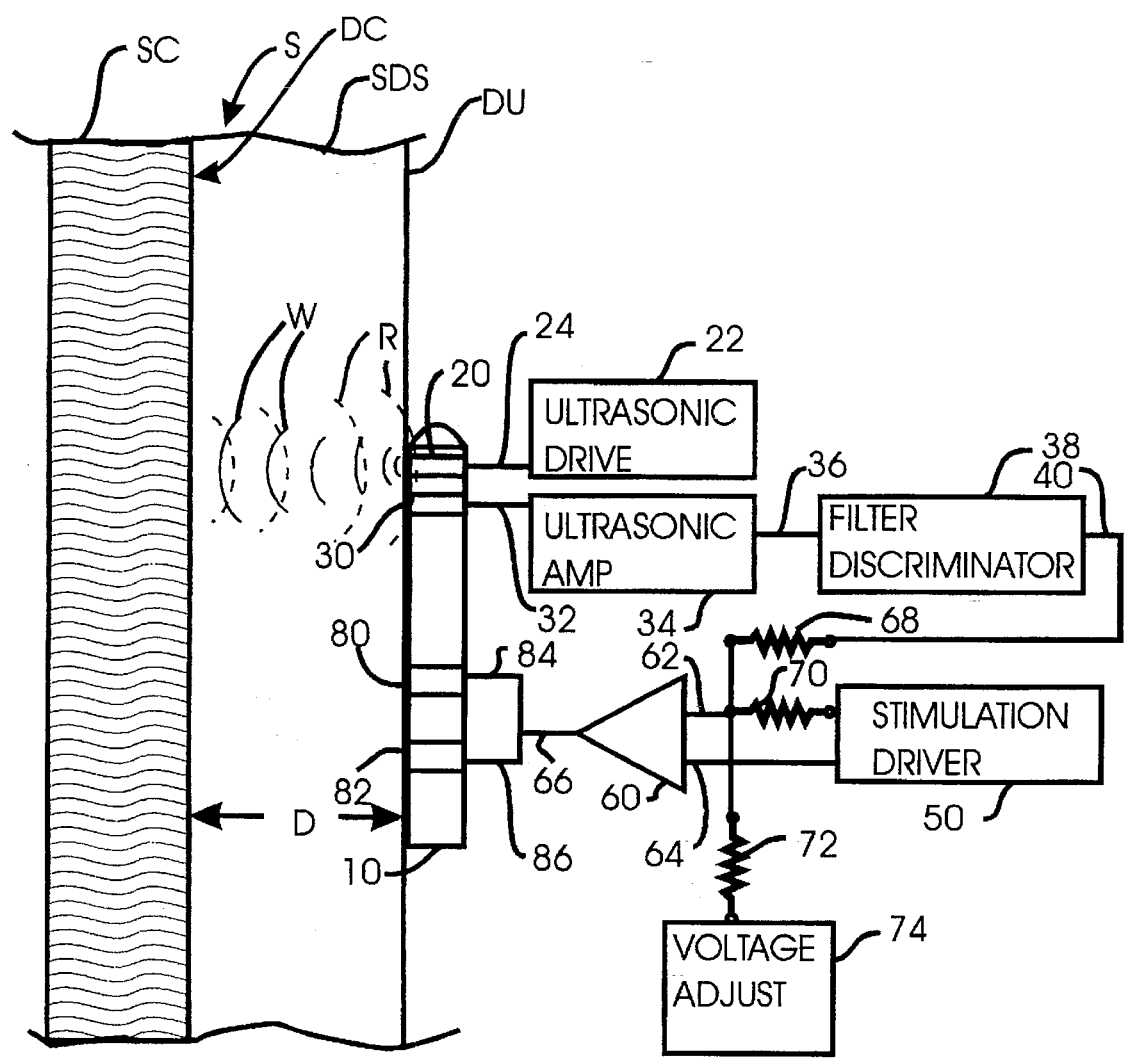
FIG. 1 is a diagrammatic representation of a preferred embodiment of the invention for stimulating tissue adjacent a spinal cord together with a representation of an exemplary spinal cord located adjacent the apparatus.
Figure 2:
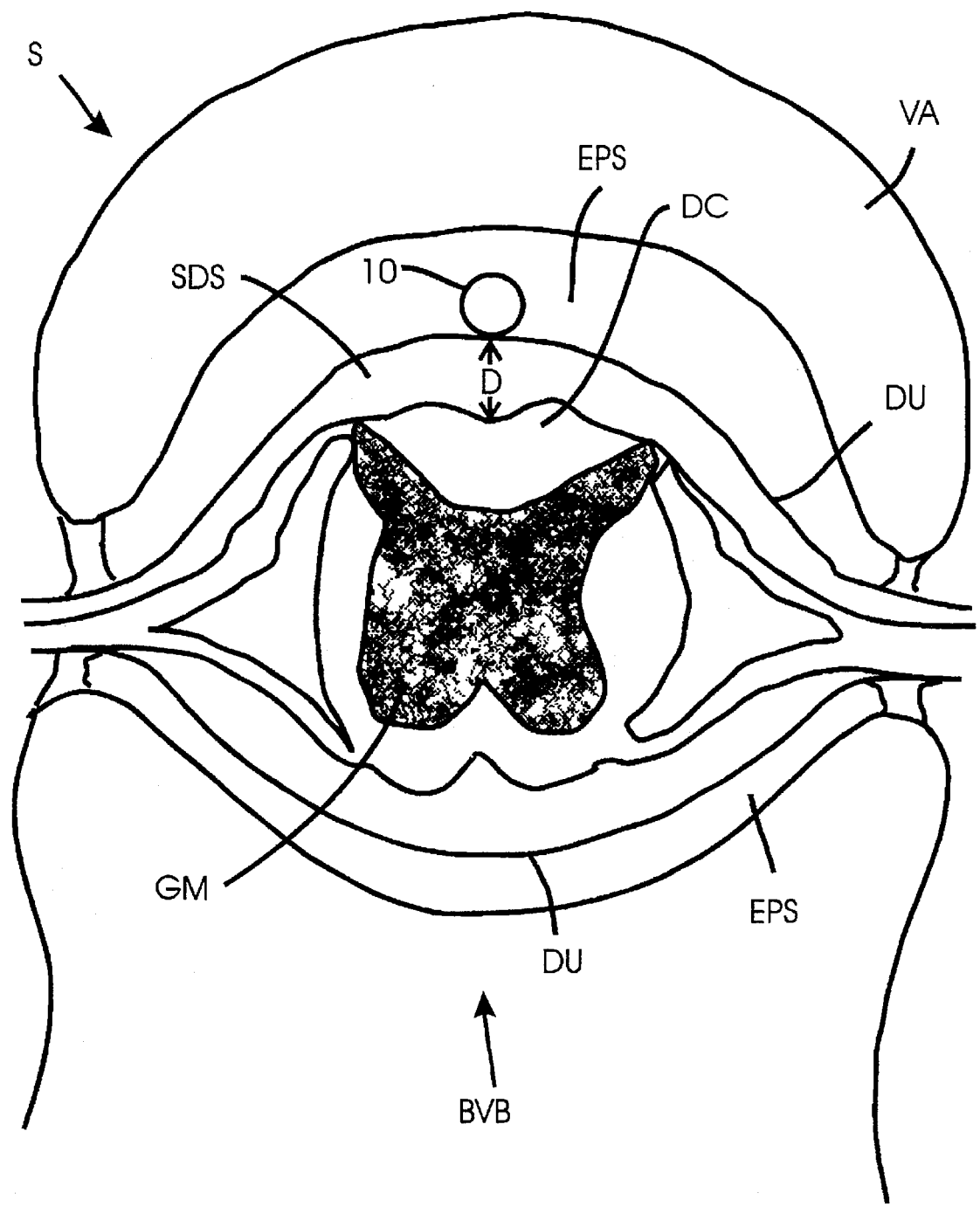
FIG. 2 is a diagrammatic cross-section of the spinal cord shown in FIG. 1 illustrating the placement of the preferred embodiment with respect to the spinal cord.

Referring to FIGS. 1 and 2, a stimulation lead 10 is placed in the epidural space EPS of a human spinal column S near the dura DU which is located at a distance D from the dorsal columns DC. The dura DU is separated from the dorsal columns by a subdural space SDS. Other parts of spinal column S include the gray matter GM, the bony vertebral body BVB and the vertebral arch VA (FIG. 2).

Lead 10 carries an ultrasonic transducer 20 capable of creating ultrasonic sound waves in response to an ultrasonic drive circuit 22 which generates an ultrasonic signal that is carried to transducer 20 over a conductor 24. Alternatively, transducer 20 could be separated from lead 10.

Ultrasonic waves W are carried through the dura and the subdural space from transducer 20 to dorsal columns DC which create corresponding reflected ultrasonic echo waves R, some of which reach a conventional ultrasonic receiver transducer 30 and cause it to create a corresponding electrical echo signal in response to the echo waves R. The echo signal is carried over a conductor 32 to an amplifier 34 which generates an amplified ultrasonic signal on a conductor 36 that is carried to a filter discriminator 38. Discriminator 38 generates a distance signal on a conductor 40 by minimizing the components of the amplified ultrasonic signal resulting from ultrasonic waves reflected from objects other than the dorsal columns. The drive signal on conductor 40 decreases in value as distance D between lead 10 and the dorsal columns increases and increases as distance D decreases.

Ultrasonic drive 22 may be operated continuously so that ultrasonic waves W are transmitted continuously towards dorsal columns DC and reflected echo waves R are continuously received by transducer 30. For this embodiment, the distance signal on conductor 40 is proportional to the amplitude of the reflected echo waves received by transducer 30.

Alternatively, ultrasonic drive 22 can be operated to produce time-spaced pulses that cause time-spaced ultrasonic waves W to be propagated toward dorsal columns DC. As a result, the reflected echo waves R also are received by transducer 30 in a time-spaced manner. In this embodiment, the amplitude of the drive signal on conductor 40 is inversely proportional to the period of reflected echo waves R, that is, the amount of time between the generation of a pulse wave by transducer 20 and the receipt of a corresponding reflected echo wave R by transducer 30. Drive 22 preferably applies a shock pulse to transducer 20. An exemplary circuit for generating such a shock pulse is described on page 97 of *Physical Principles of Ultrasonic Diagnosis*, by P. N. T. Wells (Academic Press 1969) which is incorporated by reference.

Filter discriminator 38 can be made by generating a time window and only analyzing the echo signals received during the time window. A circuit for generating such a time window is taught in "An Ultrasonic Bladder-volume Sensor", by M. T. Rise et al., *IEEE Transactions on Biomedical Engineering*, Vol. BME-26, No. 12, Dec. 1979, which is incorporated by reference.

All of components 20–40 form an ultrasonic transducer module; components 30–40 comprise an ultrasonic receiver for generating the distance signal on conductor 40.

A stimulation driver 50 is provided for generating a stimulation signal suitable for electrical stimulation of the spinal cord or adjacent tissue. Such stimulation drivers are well known in the art of electrical stimulation. For example, an exemplary stimulation driver is manufactured by Medtronic, Inc. under the trademark Itrel II.

The stimulation signal produced by driver 50 is processed by an operational amplifier 60 having a negative input 62, a positive input 64, and an output 66. Input 64 is connected to ground potential and input 62 is connected through a resistor 68 to output 40 and through a resistor 70 to the output of stimulation driver 50. Resistors 68 and 70 form with amplifier 60 a negative feedback network so that increasing amplitude of the distance signal on conductor 40 proportionately reduces the amplitude of the drive signal on output 66.

The drive signal produced on output 66 is transmitted to conventional stimulation electrodes and 82 over conductors 84 and 86.

The amplitude of the drive signal on conductor 66 also may be controlled through a resistor 72 that is connected to a conventional voltage adjustment circuit 74 accessible by a physician.

Conductors 24, 32, 84 and 86 may be located inside lead 10 and may exit the skin of the patient in whom lead 10 is implanted. In this embodiment, components 22 and 34 through 66 may be located outside lead 10 and outside the body of the patient.

Those skilled in the art will recognize that the preferred embodiments may be altered without departing from the true spirit and scope of the invention as defined in the accompanying claims.

We claim:

1. Apparatus for stimulation of a spinal cord or tissue adjacent a spinal cord located within the spinal column of a vertebrate comprising in combination:

ultrasonic transducer means adapted to be implanted adjacent said spinal cord for producing ultrasonic sound waves that create ultrasonic echo waves reflected from a predetermined portion of said spinal cord and for generating a distance signal in response to said ultrasonic echo waves, a value of said distance signal being related to a distance between said transducer means and said predetermined portion of said spinal cord;

a stimulation driver for generating a stimulation signal;

a drive amplifier responsive to said stimulation signal and said distance signal for generating a drive signal that increases in value as the distance between said transducer means and said predetermined portion increases, and decreases in value as the distance between said transducer means and said predetermined portion decreases;

at least one stimulation electrode adapted to be implanted adjacent said spinal cord; and means for transmitting said drive signal to said at least one electrode, whereby the uniformity of stimulation received by said spinal cord or adjacent tissue is increased in spite of changes in the relative distance between said transducer means and said predetermined portion of said spinal cord.

2. Apparatus, as claimed in claim 1, wherein said ultrasonic transducer means comprises:

a drive circuit for generating an ultrasonic drive signal;

an ultrasonic transmitter for producing said ultrasonic sound waves in response to said ultrasonic drive signal;

an ultrasonic receiver for generating said distance signal in response to said ultrasonic echo waves.

3. Apparatus, as claimed in claim 2, wherein said ultrasonic transmitter is operated continuously and wherein said ultrasonic receiver produces said distance signal by responding to an amplitude of the echo waves received by said ultrasonic receiver.

4. Apparatus, as claimed in claim 2, wherein said first ultrasonic transmitter is pulsed and wherein said ultrasonic receiver produces said distance signal by responding to a time delay between a production of a pulse by said ultrasonic transmitter and a receipt of a corresponding echo wave by said ultrasonic receiver.

5. Apparatus, as claimed in claim 2, wherein said receiver comprises:

an ultrasonic transducer for generating an electrical ultrasonic signal in response to said ultrasonic echo waves;

an amplifier for amplifying said ultrasonic signal to produce an amplified ultrasonic signal; and filter means responsive to said amplified ultrasonic signal for generating said distance signal by minimizing the components of said amplified ultrasonic signal resulting from ultrasonic waves reflected from objects other than said predetermined portion of said spinal cord.

6. Apparatus, as claimed in claim 1, wherein said drive amplifier comprises a first input and a second input and further comprising means for impressing said drive signal between said first and second inputs and for transmitting said distance signal to said second input so that said distance signal provides negative feedback to said drive amplifier.

7. Apparatus, as claimed in claim 1, and further comprising means accessible from outside said driver or drive amplifier for adjusting the amplitude of said drive signal.

8. A method for stimulation of a spinal cord or tissue adjacent a spinal cord located within the spinal column of a vertebrate by means of a transducer and one or more stimulation electrodes implanted adjacent said spinal cord comprising the steps of:

producing ultrasonic sound waves that create ultrasonic echo waves reflected from a predetermined portion of said spinal cord;

generating a distance signal in response to said ultrasonic echo waves, a value of said distance signal being related to a distance between said transducer and said predetermined portion of said spinal cord;

generating a stimulation signal;

generating a drive signal responsive to said stimulation signal and said distance signal, said drive signal increasing in value as the distance between said transducer and said predetermined portion increases, and decreasing in value as the distance between said transducer and said predetermined portion decreases; and transmitting said drive signal to said at least one stimulation electrode, whereby the uniformity of stimulation received by said spinal cord or adjacent tissue is increased in spite of changes in the relative distance between said transducer and said predetermined portion of said spinal cord.

9. A method, as claimed in claim 8, wherein said step of producing ultrasonic sound waves comprises:

generating an ultrasonic drive signal; and producing said ultrasonic sound waves in response to said ultrasonic drive signal.

10. A method, as claimed in claim 9, wherein said step of generating an ultrasonic drive signal comprises the step of generating said drive signal continuously and wherein said step of generating said distance signal comprises the step of responding to an amplitude of said echo waves.

11. A method, as claimed in claim 9, wherein said step of generating an ultrasonic drive signal comprises the step of generating a pulse signal and wherein said step of generating said distance signal comprises the step of responding to a time delay between a production of said pulse signal and a receipt of a corresponding echo wave.

12. A method, as claimed in claim 11, wherein said step of generating said distance signal comprises the step of generating a time window during a time period in which said corresponding echo wave is received by said transducer so that an effect of echo waves received outside said time window is minimized.

* * * * *

UNITED STATES PATENT AND TRADEMARK OFFICE
CERTIFICATE OF CORRECTION

PATENT NO. :    5,628,317
DATED      :    May 13, 1997
INVENTOR(S) :   Starkebaum et al.

It is certified that error appears in the above-identified patent and that said Letters Patent is hereby corrected as shown below:

Col. 4, Line 55:   "one or more stimulation electrodes" should be "at least one stimulation electrode"

Col. 3, Line 35:   "and 82" should be "80 and 82"

Col 1., Line 7:    "relates" should be "relates to"

Signed and Sealed this

Seventh Day of October, 1997

Attest:

BRUCE LEHMAN

*Attesting Officer*    *Commissioner of Patents and Trademarks*